US 8,391,648 B2
Mar. 5, 2013

(12) United States Patent
Janes

(54) IMAGING SYSTEM FOR COMPENSATING FOR MASK FRAME MISALIGNMENT

(75) Inventor: David Janes, Rolling Meadows, IL (US)

(73) Assignee: Siemens Medical Solutions USA, Inc., Malvern, PA (US)

(*) Notice: Subject to any disclaimer, the term of this patent is extended or adjusted under 35 U.S.C. 154(b) by 1013 days.

(21) Appl. No.: 12/412,552

(22) Filed: Mar. 27, 2009

(65) Prior Publication Data
US 2010/0074483 A1 Mar. 25, 2010

Related U.S. Application Data

(60) Provisional application No. 61/040,249, filed on Mar. 28, 2008.

(51) Int. Cl.
G06K 9/32 (2006.01)
(52) U.S. Cl. ........................................ 382/299; 382/132
(58) Field of Classification Search .................. 382/132, 382/299
See application file for complete search history.

(56) References Cited

U.S. PATENT DOCUMENTS

| 5,304,806 | A | 4/1994 | Hines et al. |
| 5,378,915 | A * | 1/1995 | Hines et al. ................ 250/369 |
| 7,127,684 | B2 | 10/2006 | Morita et al. |
| 2004/0100477 | A1 | 5/2004 | Morita et al. |
| 2004/0100503 | A1 | 5/2004 | Morita et al. |
| 2006/0239524 | A1 | 10/2006 | Desh et al. |
| 2007/0030946 | A1 * | 2/2007 | Tsuyuki et al. ................ 378/8 |

OTHER PUBLICATIONS

DICOM, Digital Imaging and Communications in Medicine (DICOM), Part 3: Information Object Definitions, PS Mar. 3, 2008, National Electrical Manufacturers Association, Rosslyn, Virginia.
DICOM, Digital Imaging and Communications in Medicine (DICOM), Part 6: Data Dictionary, PS Mar. 6, 2001, National Electrical Manufacturers Association, Rosslyn, Virginia.

* cited by examiner

Primary Examiner — Howard Weiss
Assistant Examiner — Tifney Skyles
(74) Attorney, Agent, or Firm — Alexander J Burke

(57) ABSTRACT

An imaging system compensates for mask frame misalignment with non-mask frames in an image sequence of patient anatomy. The system includes an image data processor. The image data processor determines a compensation zoom factor for individual image frames of an image sequence of an object of interest in response to data indicating distance between the object and a radiation detector for the individual image frames. The processor then associates individual zoom factors with corresponding individual image frames of the image sequence. The individual zoom factors associated with corresponding individual image frames of the image sequence are stored in a repository. An individual determined zoom factor is applied to align an associated corresponding image frame with a mask frame to provide an aligned image frame. Data representing an image difference frame, comprising a difference between data representing the aligned image frame and a mask frame, is determined. A user interface generates data representing a display image presenting the image difference frame.

18 Claims, 4 Drawing Sheets

IMAGING SYSTEM FOR COMPENSATING FOR MASK FRAME MISALIGNMENT

CROSS-REFERENCE TO RELATED APPLICATION

This application is a non-provisional application of Application Ser. No. 61/040,249 filed 28 Mar. 2008 by D. Janes.

BACKGROUND OF THE INVENTION

1. Field of the Invention

The present invention relates to an imaging system, and in particular an X-Ray imaging system, which provides a frame subtraction feature in order to enhance images produced by such a system.

2. Description of the Related Art

Imaging systems are used to allow users to analyze objects using optical, or other scanning means which may be converted to an image display. In some situations, the difference between a first image frame and one or more other image frames is of interest to the user.

For example, a medical imaging system, and in particular an X-Ray imaging system, is often used to analyze blood vessels within a patient. In such a situation, a dye which is substantially opaque to X-Rays is injected into the patient to be pumped to the desired blood vessels within the body. A sequence of X-Ray frames is taken of the desired area of the body to detect the entry and path of the dye within the blood vessels, and thus to display for the user an image of the size and location and operation of the blood vessels in that area. However, image artifacts produced by other parts of the body in the area being observed can obscure or otherwise distract the user from the primary goal of analyzing the blood vessels. Referring to FIG. 1, the center image 104 is an example of such an image.

Systems exist which will select an image frame of the desired area during the time before the dye is detected. Such an image frame is termed a mask frame in the present application and represents a background or quiescent image of the area of interest. Referring again to FIG. 1, the right hand image 106 represents a mask frame. This mask frame is saved, and subtracted from the respective subsequent sequence of image frames, sometimes termed fill frames, showing the dye entering and leaving the desired area. By subtracting a 'non-dye' image from the subsequent 'dye' image, the image of the other body parts is minimized, leaving only the image of the dye in the blood vessel. Referring again to FIG. 1, the left hand image 102 represents this 'difference' image. In image 102, artifacts representing the surrounding anatomical features are minimized, and the blood vessels, highlighted by the dye, are more easily seen and analyzed. This is termed a frame subtraction feature in the present application.

More generally, in such imaging systems, a mask frame may be designated and stored at a time before or after a particular test is performed, although typically the mask frame is taken at a time immediately before the sequence of image frames showing the test results. The mask frame is subtracted from the respective sequence of frames which are taken during the test. This will generate a sequence of frames in which the differences between the area of interest during a test and the area of interest before (or after) the test are highlighted, allowing a user to more easily see the results of the test.

However, it is also sometimes desirable to move the X-ray source and detector (typically rigidly attached via a C-arm) with respect to the patient, or to move the table on which the patient is laying, during the course of the test, e.g. to follow an observed anomaly or improve the view of the desired area. If the C-arm and/or table is moved while maintaining the same relative spacing of the patient between the X-ray source and the detector, then the respective locations of the subsequent sequence of frames taken during a test is offset from the location at which the mask frame was taken. This may be compensated for by shifting the mask frame so that the mask frame remains aligned with the respective sequence of subsequent images.

For example, during the test, the C-arm and/or the table on which the patient is lying may be moved. The imaging system maintains data representing position of the table and the position of the C-arm. The table position and C-arm position data at the time of each image frame is stored with the image data representing that image frame. During display of the X-ray image frames, the orientation and/or position data is retrieved for the respective subsequent image frames and the mask frame shifted the appropriate amount to maintain the alignment with the subsequent sequence of frames.

However, it may be further desirable to change the position of the patient closer to or farther away from the imaging system detector. This results in a sequence of images which is relatively enlarged or reduced, i.e. zoomed. In this situation, the mask frame which was previously taken and saved no longer represents an accurate representation of the background or quiescent image as presented in the subsequent sequence of images. Subtracting such a mask frame from the subsequent sequence of images will not result in highlighting the test results by minimizing the background or quiescent image, and may even result in obscuring the test results.

FIG. 2 is an X-ray image illustrating the difference between a mask frame and a fill image frame which has been zoomed with respect to the mask frame. In FIG. 2, a mask frame is taken and stored with the subject at a first distance between the X-ray source and detector, and a fill frame is taken with the same subject at a second distance between the X-ray source and detector. More specifically, the image of FIG. 2, shows a motor 202 and a small round disk 204. The motor 202$m$ appears light and the disk 204$m$ appears white in the mask frame, and the motor 202$f$ and the disk 204$f$ appear black in the subsequent fill frame. As may be seen, the image of the motor 202$m$ and disk 204$m$ appear smaller in the mask frame than in the fill frame, 202$f$, 204$f$. In addition, the images of the motor 202$m$ and disk 204$m$ in the mask frame are displaced from the respective images of the motor 202$f$ and disk 204$f$ in the fill frame. This implies that the mask frame was taken and stored while the subjects, e.g. motor 202 and disk 204, were further from the detector than when the fill frame was taken. It may be seen that the mask frame does not correspond in size with the fill frame and, therefore, is misaligned with non-mask image. Consequently, the resulting subtraction frame illustrated in FIG. 2 does not accurately eliminate background and/or quiescent artifacts. It may also be seen that there is no amount of frame shifting (described above) which will bring the mask frame image and fill frame image into alignment.

An imaging system is desirable which will permit a frame subtraction feature to be used when a patient is moved closer to or further from the detector in the imaging system in the manner described above.

SUMMARY OF THE INVENTION

An image of the kind generated by an imaging system may be characterized inter alia by its resolution. When a subject is closer to or further from a detector in such an imaging system, the resolution of the resulting image changes. More specifically, each pixel of the image frame represents a linear distance in the imaged subject. In the present application, resolution of an image is represented by the number of millimeters per pixel. When a subject is closer to the detector, each pixel in the image represents fewer millimeters and when a subject is farther from the detector, each pixel in the image represents more millimeters. The resolution of an image frame may be represented by a compensation zoom factor for that image frame with respect to a predetermined zoom factor at a corresponding predetermined distance between the source and detector in an imaging system.

The inventor has advantageously determined that if the location of the imaged subject between the source and detector of the imaging system is known, or may be calculated, the resolution and/or compensation zoom factor may be also be calculated, and that if the respective compensation zoom factors of a mask frame and a subsequent fill frame are both known, these zoom factors may be used to adjust the mask frame so that it has the same resolution as the subsequent fill frame. The adjusted mask frame may be subtracted from the subsequent fill frame to minimize background and/or quiescent artefacts in the resulting image.

In accordance with principles of the present invention an X-ray imaging system compensates for mask frame misalignment with non-mask frames in an X-ray image sequence of patient anatomy. The system includes an image data processor. The image data processor determines a compensation zoom factor for individual image frames of an X-ray image sequence of patient anatomy in response to data indicating distance between a patient table and an X-ray radiation detector for the individual image frames. The processor associates individual zoom factors with corresponding individual image frames of the X-ray image sequence. The individual zoom factors associated with corresponding individual image frames of the X-ray image sequence are stored in a repository. More specifically, the individual zoom factors are stored as private data with the associated image. An individual determined zoom factor is applied to align an associated corresponding image frame with a mask frame to provide an aligned image frame. Data representing an image difference frame, comprising a difference between data representing the aligned image frame and a mask frame, is determined. A user interface generates data representing a display image presenting the image difference frame.

DETAILED DESCRIPTION OF THE PREFERRED EMBODIMENTS

A processor, as used herein, operates under the control of an executable application to (a) receive information from an input information device, (b) process the information by manipulating, analyzing, modifying, converting and/or transmitting the information, and/or (c) route the information to an output information device. A processor may be configured to comprise a special purpose computer herein performing functions not performable by a general purpose computer. A processor may use, or comprise the capabilities of, a controller or microprocessor, for example. The processor may operate with a display processor or generator. A display processor or generator is a known element for generating signals representing display images or portions thereof. A processor and a display processor comprises any combination of, hardware, firmware, and/or software.

An executable application, as used herein, comprises code or machine readable instructions for conditioning the processor to implement predetermined functions, such as those of an operating system, imaging system or other information processing system, for example, in response to user command or input. An executable procedure is a segment of code or machine readable instruction, sub-routine, or other distinct section of code or portion of an executable application for performing one or more particular processes. These processes may include receiving input data and/or parameters, performing operations on received input data and/or performing functions in response to received input parameters, and providing resulting output data and/or parameters.

A user interface (UI), as used herein, comprises one or more display images, generated by the display processor under the control of the processor. The UI also includes an executable procedure or executable application. The executable procedure or executable application conditions the display processor to generate signals representing the UI display images. These signals are supplied to a display device which displays the image for viewing by the user. The executable procedure or executable application further receives signals from user input devices, such as a keyboard, mouse, light pen, touch screen or any other means allowing a user to provide data to the processor. The processor, under control of the executable procedure or executable application, manipulates the UI display images in response to the signals received from the input devices. In this way, the user interacts with the display image using the input devices, enabling user interaction with the processor or other device. A graphical user interface (GUI) uses graphical display images, as opposed to textual display images, when generating the UI.

Figure 3:
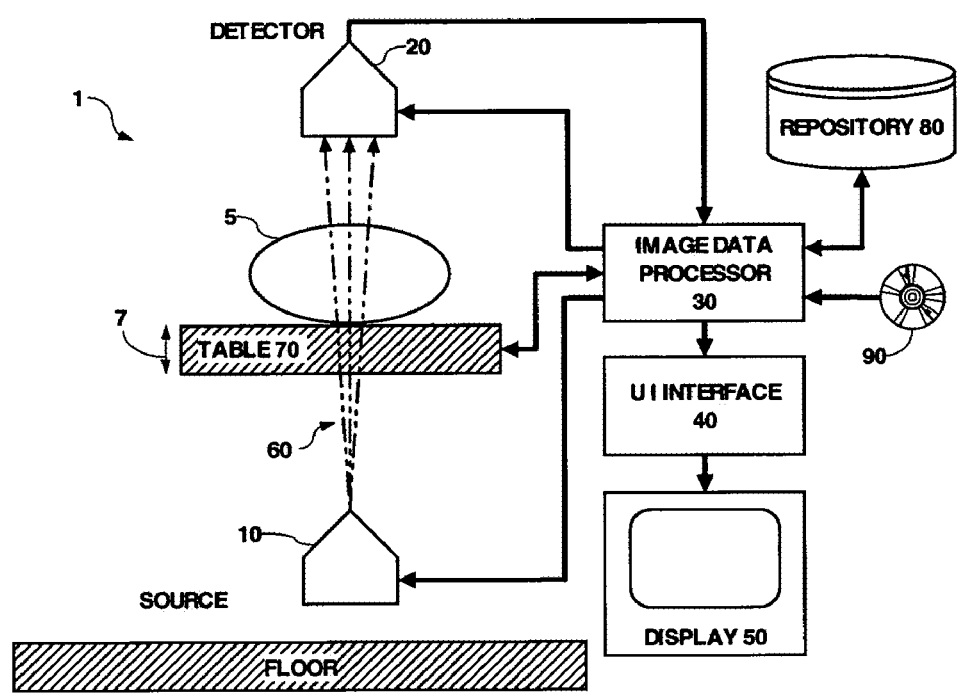
FIG. 3 is a diagram partially in schematic form and partially in block form of an imaging system according to principles of the present invention.

FIG. 3 illustrates an embodiment of an imaging system 1 according to principles of the present invention. In FIG. 3, respective control output terminals of an image data processor 30 are coupled to corresponding control input terminals of an X-ray source 10 and X-ray detector 20. The X-ray source 10 produces X-rays 60 which are detected by detector 20 after passing through a patient 5. The X-rays received by the detector 20 represent data describing internal anatomy of the patient 5. In the embodiment described in the present invention, the internal anatomical feature of interest comprises blood vessels. One skilled in the art understands that any anatomical feature of the patient may be analyzed using the imaging system 1 of the present application. Data representing an image produced by detected X-rays by detector 20 is provided to a data input terminal of the image data processor 30. A bidirectional data terminal of the image data processor 30 is coupled to a corresponding data terminal of a repository 80, and an input terminal of the image data processor 30 is coupled to a data storage device 90. This is illustrated schematically in FIG. 3 as a CD, however, one skilled in the art understands that any storage device which can store data, either as volatile or non-volatile storage, and either as read-only or read/write, and which can provide data stored on it to the image data processor 30 may be used. Examples of such data storage devices are hard disk drives, CD and DVD players, floppy disk drives, solid-state memory, such as memory sticks, etc. A data output terminal of the image data processor 30 is coupled to an input terminal of a user interface (UI) interface 40. An output terminal of the UI interface 40 is coupled to an input terminal of a display device 50. Another control output terminal of the image data processor 30 is coupled to a corresponding control input terminal of a table 70 on which the patient 5 is laying.

In operation, image data processor 30 may execute data representing executable applications (executable code and associated data) from the data storage device 90 and may store data on and retrieve data from repository 80. During testing operations, the X-rays 60 passing through the patient 5 produce X-rays at the detector 20 which represent information about an anatomical feature of interest within the patient 5, in a known manner. Typically, the X-ray source 10 and X-ray detector 20 are rigidly attached to each other, and may be moved and/or rotated around the patient as a unit. The data representing the received X-rays at the detector 20 are processed by the image processor 30 to produce data representing a display image (FIG. 1 and FIG. 2) illustrating the anatomical feature of interest within the patient 5. For example, a user of the system 1 may be interested in vessels surrounding the heart of the patient 5. The user uses the UI interface 40 to control the X-ray source 10 to generate X-rays of the desired energy, through the appropriate portion of the patient, at the appropriate angle to generate an image of the vessels. The user also uses the UI interface to control the X-ray detector 20 to receive the X-rays 60 produced by the X-ray source 10 and passing through the patient 5 and provide data representing an X-ray image to the image data processor 30. The image data processor 30 then processes the data received from the detector 20 and produces corresponding data representing an image of the vessels surrounding the heart of the patient 5 (FIG. 1), in a known manner.

In accordance with principles of the present invention, an imaging system 1 compensates for mask frame misalignment with non-mask frames in an image sequence. As described in detail herein, such a system may be an X-ray imaging system 1 producing a sequence of images of patient 5 anatomy. The system includes image data processor 30. The image data processor 30, which includes a processor and associated executable application, determines a compensation zoom factor for individual image frames of an image sequence of an object of interest (patient 5) in response to data indicating distance between the object (patient 5) and a radiation detector 20 for the individual image frames. More specifically, the image data processor 30 determines a compensation zoom factor for individual frames of an X-ray image sequence of patient anatomy in response to data indicating distance between a patient table 70 and an X-ray radiation detector 20 for the individual image frames.

Further, the image data processor 30 determines a compensation zoom factor for each individual image frame of an image sequence of patient 5 anatomy in response to determination of distance between a patient table 70 and a radiation detector 20 for each individual image frame. The image data processor 30 determines the compensation zoom factor for individual image frames of the X-ray image sequence of patient anatomy further in response to data indicating distance between the X-ray radiation detector 20 and an X-ray emitter 10. As described in more detail below, the angle of the X-ray detector 20 with respect to the patient support table 70 and/or the X-ray emitter source 10 may be changed. In such a case, the image data processor 30 determines the compensation zoom factor for individual image images of the X-ray image sequence of patient anatomy in response to data indicating an angle of the X-ray radiation detector relative to at least one of: (a) a patient support table and (b) an X-ray emitter.

The image data processor 30 associates individual zoom factors with corresponding individual image frames of the image sequence and stores the individual zoom factors associated with corresponding individual image frames of the image sequence in repository 80. More specifically, the image data processor 30 stores the individual zoom factors associated with corresponding individual image frames in a private section of a 'digital imaging and communication in medicine' (DICOM) compatible image data file structure.

The image data processor 30 applies an individual determined zoom factor to align an associated corresponding image frame and a mask frame to provide an aligned image frame. Processor 30 determines data representing an image difference frame comprising a difference between data representing the aligned image frame and a mask frame. A user interface 40 generates data representing a display image presenting the image difference frame on a display 50.

Figure 1:
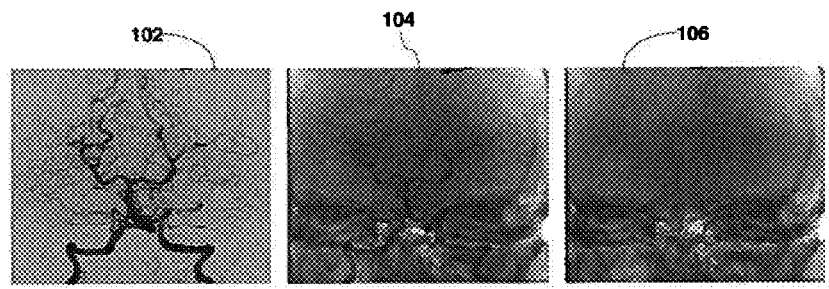
FIG. 1 is a set of X-ray images illustrating the frame subtraction feature of the present invention.
Figure 2:
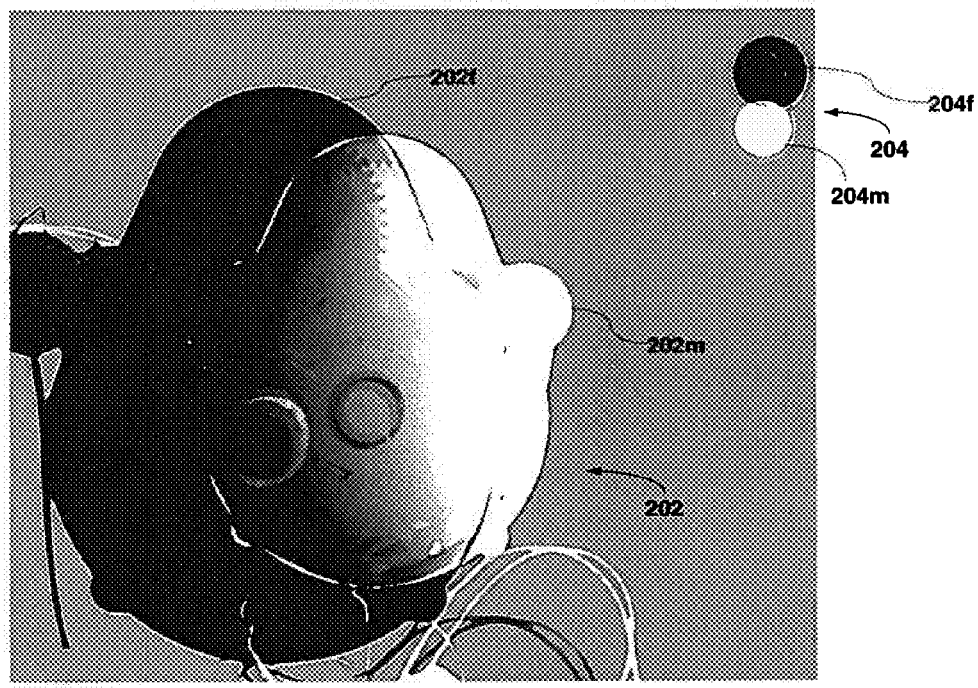
FIG. 2 is an X-ray image illustrating a frame subtraction image resulting from moving the table on which objects are placed closer to the detector of the imaging system.

As described above, a mask frame may be taken before an anatomical event of interest, such as introduction of a dye into a blood vessel. The mask frame 106 may be saved and subtracted from respective ones of the subsequent sequence of image frames which show the blood vessels with the dye in them. FIG. 1 illustrates a mask frame 106 and one fill frame 104 and the corresponding difference frame 102. One skilled in the art understands that a sequence of fill frames, e.g. 104, may be taken and a mask frame, e.g. 106, subtracted from the respective image frames in the sequence of fill frames. The resulting sequence of difference frames, e.g. 102, may be analyzed by a user individually, or replayed as a group in a manner similar to a movie, video clip, or animation.

Figure 4:
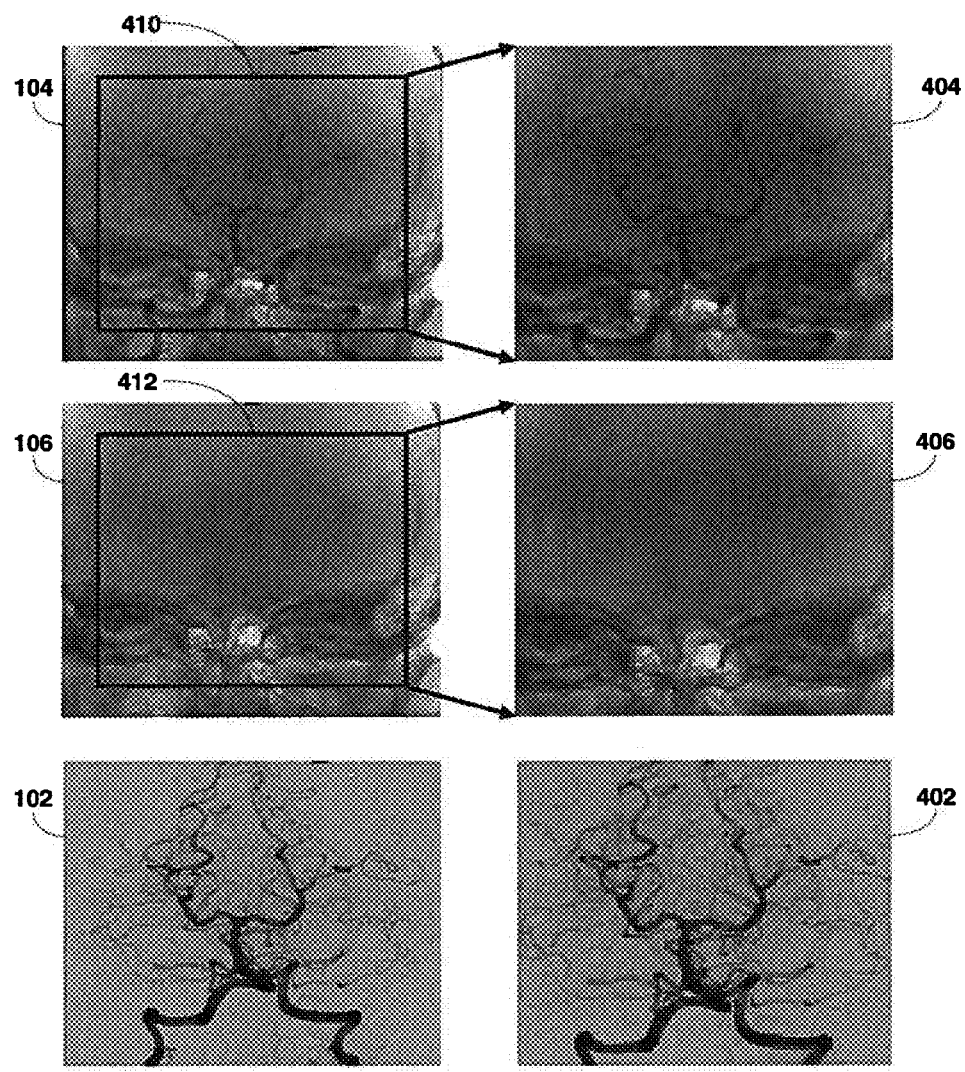
FIG. 4 is a set of X-ray images corresponding to those of FIG. 1 illustrating the operation of the imaging system in response to zooming in accordance with principles of the present invention.

However, also as described above, it may be desirable to move the table 70 on which the patient 5 is laying closer to or further from the detector 20, i.e. to zoom in or out respectively. If the table is raised, the image is zoomed in; if the table is lowered, the image is zoomed out. FIG. 4 is a set of X-ray images illustrating zooming. Referring to FIG. 4, images 102, 104 and 106 correspond to the images illustrated in FIG. 1. During operation of the imaging system 1 (FIG. 3), the table 70 is moved to move the patient 5 closer to the detector 20, i.e. upward. Because the subject patient 5 is closer to the detector 20, the image produced by the detector 20 is enlarged. The image 404 represents this image. The rectangle 410 overlaying the image 104 illustrates the portion of the image 104 displayed in the image 404.

Figure 5:
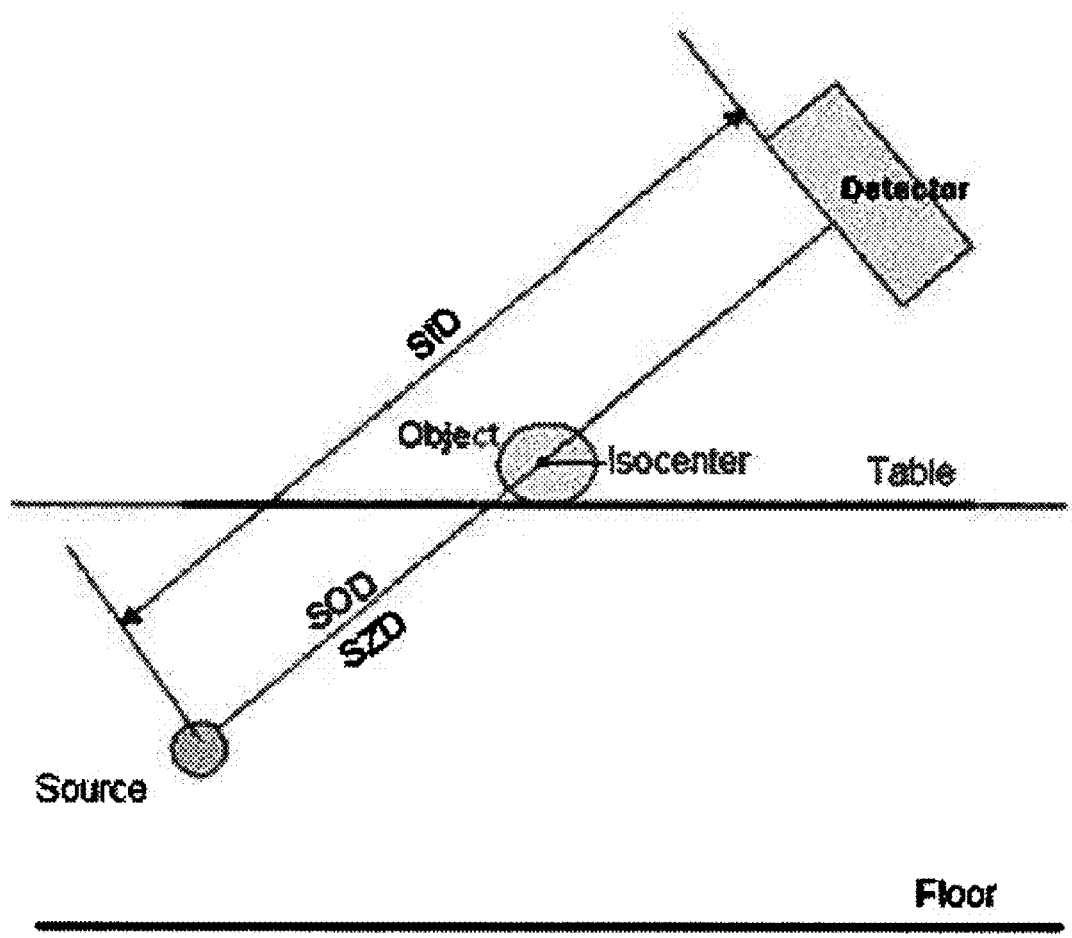
FIG. 5 is a diagram in schematic form useful in understanding the calculation of compensation and distortion zoom factors in accordance with principles of the present invention.

In the illustrated embodiment, the X-ray source 10 (FIG. 3) and X-ray detector 20 may be rotated with respect to the patient 5. The compensation zoom factor of the image frame may be calculated based on the distance between the patient and X-ray detector, and the angle of the X-ray source and X-ray detector with respect to the patient. FIG. 5 is a set of diagrams in schematic form useful in understanding the calculation of compensation and distortion zoom factors in accordance with principles of the present invention. FIG. 5 illustrates a case in which the object of interest is located along the direct line between the X-ray source and X-ray detector and is located at the isocenter, i.e. the point in space where radiation beams intersect when the X-ray source and detector is rotated during operation. In this case the compensation zoom factor M is:

$$M = \frac{SID}{SOD} \quad (1)$$

where

SID is the Source (Focus)-Detector Distance; and

SOD is the Source-Object Distance.

One skilled in the art understands that other equations may be derived and used for other cases.

Data representing the compensation zoom factor M is stored with the respective image frames taken by the detector 20 (FIG. 1) and processed by the image data processor 30.

Referring again to FIG. 4, if the previous mask frame 106 is used as a mask for the new image 404, it will not accurately minimize the background and/or quiescent artifacts. In order to accurately minimize such artifacts, the mask image 106 must also be zoomed in the same manner as the new image 404. This is done by comparing the compensation zoom factor $M_m$ for the previously stored mask with the compensation zoom factor $M_f$ for the associated fill frame. More specifically, the individual zoom factor Z required to align an associated corresponding image fill frame and a mask frame to provide an aligned image frame is the quotient:

$$Z = M_m / M_f \quad (4)$$

One skilled in the art understands that there are many algorithms for zooming image data and understands the aspects, issues and tradeoffs involved in selecting one of the algorithms. An appropriate zooming algorithm is selected by one skilled in the art and implemented as an executable procedure in image data processor 102 (FIG. 1) to perform the zooming of the mask frame. Is it also possible to implement an executable procedure in the image data processor 102 to select an appropriate zooming algorithm from among a plurality of zooming algorithms made available for use by the image data processor 102.

In FIG. 4 a zooming factor Z is applied to the mask image 106 to zoom in to the same resolution as the fill image frame 404. In FIG. 4, a rectangle 412 illustrates the portion of the original mask frame 106 which is zoomed in on to produce the zoomed mask frame 406. It may be seen that the portion of the fill image frame 104 and mask frame 106 correspond to each other. When the image data processor 30 (FIG. 1) subtracts the mask frame 406 from the fill image frame 404, a zoomed difference frame 402 is produced in which the background and/or quiescent data is minimized.

As described above, typically, the X-ray source 10 and X-ray detector 20 are aligned and rigidly attached to each other, and are moved and/or rotated around the patient as a unit. However, it is possible for the X-ray source 10 and X-ray detector 20 to fall out of alignment with each other. That is, one side of the detector 20 may be closer to the source 10 than the other side. In such a case, images produced by the imaging system is distorted. The distortion may include a tilt factor, a trapezoidal factor and/or a rotation factor. The system described above is adaptable to be used to compensate for such distortion factors. In operation, the image data processor 30 determines a compensation distortion factor for individual image frames of an X-ray image sequence of patient anatomy in response to data indicating an angle of the X-ray radiation detector relative to at least one of: (a) a patient support table and (b) an X-ray emitter. More specifically, the compensation distortion factor represents at least one of: (a) a tilt factor representing tilt of an image, (b) a trapezoidal factor representing trapezoidal distortion of an image and (c) a rotation factor representing rotation of an image.

In order to compensate for distortion of this kind, image processor 30 may partition the image into a plurality of areas. Each area is assigned a partition zoom factor calculated to compensate for the difference between the position of the portion of the detector 20 corresponding to that partition relative to the source 10 and the desired, or ideal, position of that portion of the detector 20 relative to the source 10. As each image frame is processed, the respective compensation distortion factors for the different partitions of the image may be applied to minimize the distortion.

Data representing the operations described above may be stored on a memory device, such as a CD, or DVD or any other appropriate storage device which may be read by the data storage device 90 of FIG. 3. Such data may include processor readable executable code capable of controlling the image data processor 30 to implement the above operations, and also any data associated with the executable code. The image data processor 30 can read such data and execute the executable procedure represented by that code.

The embodiment described above is described in terms of zooming the mask frame to match the zoom factor of the respective subsequent fill image frames in order to perform the frame subtraction feature accurately. One skilled in the art understands that the image data processor 30 may also zoom the respective subsequent fill image frames to match the zoom factor of the mask frame. In this case, the user interface fractionally adjusts the zoom factor of the fill frame during post-processing to match that of the mask frame.

The embodiment illustrated and described above relates to a medical imaging system and more specifically to a medical X-ray imaging system. However, one skilled in the art will understand that any imaging system which uses a frame subtraction feature to minimize background and/or quiescent image data from an image, and which may produce images which may be zoomed in or out during operation may use the invention as described above. For example, industrial imaging systems used for quality control may use the present invention.

What is claimed is:

1. An imaging system for compensating for mask frame misalignment with non-mask frames in an image sequence, comprising:

an image data processor for:

determining a compensation zoom factor for individual image frames of an image sequence in response to data indicating distance between an object of interest and a radiation detector for said individual image frames, associating individual zoom factors with corresponding individual image frames of said image sequence, storing said individual zoom factors associated with corresponding individual image frames of said image sequence in a repository, applying an individual determined zoom factor to align an associated corresponding image frame and a mask frame comprising an image frame of the image sequence prior to detection of contrast agent, to provide an aligned image frame; and determining data representing an image difference frame comprising a difference between data representing said aligned image frame and a mask frame; and a user interface for generating data representing a display image presenting said image difference frame.

2. A system according to claim 1 wherein the imaging system is an X-ray imaging system.

3. A system according to claim 2 wherein the image data processor determines a compensation zoom factor for individual frames of an X-ray image sequence of patient anatomy in response to data indicating distance between a patient table and an X-ray radiation detector for said individual image frames.

4. A system according to claim 2, wherein said image data processor determines said compensation zoom factor for individual image frames of said X-ray image sequence of patient anatomy in response to data indicating distance between said X-ray radiation detector and an X-ray emitter.

5. A system according to claim 2, wherein said image data processor determines a compensation zoom factor for each individual image frame of an X-ray image sequence of patient anatomy in response to determination of distance between a patient table and an X-ray radiation detector determined for said each individual image frame.

6. A system according to claim 2 wherein the image data processor determines a compensation zoom M factor for individual frames on an X-ray image sequence according to the equation:

$$M = \frac{SID}{SOD}$$

where
SID is the Source (Focus)-Detector Distance; and
SOD is the Source-Object Distance.

7. A system according to claim 2, wherein said image data processor determines said compensation zoom factor for individual image frames of said X-ray image sequence of patient anatomy in response to data indicating an angle of said X-ray radiation detector relative to at least one of, (a) a patient support table and (b) an X-ray emitter.

8. A system according to claim 2 wherein said image data processor applies an individual determined zoom factor to align an associated corresponding image frame and a mask frame in response to the data representing said individual determined zoom factor and a determined zoom factor for said mask frame.

9. A system according to claim 8 wherein the image data processor:
generates a mask zoom factor in response to said individual determined zoom factor for an associated corresponding image frame and said individual determined zoom factor for said mask frame; and
applies said mask zoom factor to the mask frame to produce an aligned mask frame.

10. A system according to claim 9 wherein the image data processor generates said mask zoom factor Z according to the equation:

$$Z = M_m/M_f$$

where
$M_m$ is the individual determined zoom factor for the mask frame; and
$M_f$ is the individual determined zoom factor for the associated corresponding image frame.

11. A system according to claim 10 wherein the image data processor:
generates respective image frame zoom factors in response to the individual determined zoom factors for the respective image frames and said individual determined zoom factor for said mask frame; and
applies said respective image frame zoom factors to the respective image frames to produce an aligned mask frame.

12. A system according to claim 11 wherein the image data processor generates said respective image frame zoom factors Z according to the equation:

$$Z = M_f/M_m$$

where
$M_m$ is the individual determined zoom factor for the mask frame; and
$M_f$ is the individual determined zoom factor for the respective associated corresponding image frames.

13. A system according to claim 11 wherein the image data processor determines data representing an image difference frame comprising the difference between data representing said image frame and said aligned mask frame.

14. A system according to claim 2, wherein said image data processor determines a compensation distortion factor for individual image frames of an X-ray image sequence of patient anatomy in response to data indicating an angle of said X-ray radiation detector relative to at least one of, (a) a patient support table and (b) an X-ray emitter.

15. A system according to claim 1, wherein said image data processor stores said individual zoom factors associated with corresponding individual image frames in a private section of a DICOM compatible image data file structure.

16. A system according to claim 1, wherein said compensation distortion factor comprises at least one of, (a) a tilt factor representing tilt of an image, (b) a trapezoidal factor representing trapezoidal distortion of an image and (c) a rotation factor representing rotation of an image.

17. A system according to claim 1, including a user-interface enabling a user to fractionally adjust zoom of at least one of, (a) an individual image frame and (b) a mask frame during image post-acquisition processing.

18. A method employed by an imaging system for compensating for mask frame misalignment with non-mask frames in an image sequence, comprising the activities of:
determining a compensation zoom factor for individual image frames of an image sequence in response to data indicating distance between an object of interest and a radiation detector for said individual image frames,
associating individual zoom factors with corresponding individual image frames of said image sequence,
storing said individual zoom factors associated with corresponding individual image frames of said image sequence in a repository,
applying an individual determined zoom factor to align an associated corresponding image frame and a mask frame comprising an image frame of the image sequence prior to detection of contrast agent, to provide an aligned image frame;
determining data representing an image difference frame comprising a difference between data representing said aligned image frame and a mask frame; and
generating data representing a display image presenting said image difference frame.

* * * * *